(12) United States Patent
Leff et al.

(10) Patent No.: US 10,869,699 B2
(45) Date of Patent: *Dec. 22, 2020

(54) ROD LINK REDUCER

(71) Applicant: GLOBUS MEDICAL, INC., Audubon, PA (US)

(72) Inventors: David Leff, Philadelphia, PA (US); Sergio Muniz, Philadelphia, PA (US); Khiem Pham, Chalfont, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/167,697

(22) Filed: Oct. 23, 2018

(65) Prior Publication Data

US 2019/0053835 A1    Feb. 21, 2019

Related U.S. Application Data

(63) Continuation of application No. 15/265,083, filed on Sep. 14, 2016, now Pat. No. 10,136,928.

(51) Int. Cl.
*A61B 17/70* (2006.01)

(52) U.S. Cl.
CPC ........ *A61B 17/7086* (2013.01); *A61B 17/705* (2013.01); *A61B 17/708* (2013.01); *A61B 17/7049* (2013.01); *A61B 17/7079* (2013.01)

(58) Field of Classification Search
USPC ........................................................ 606/59
See application file for complete search history.

(56) References Cited

U.S. PATENT DOCUMENTS

| | | | |
|---|---|---|---|
| 7,314,331 B1* | 1/2008 | Koros | A61B 90/57 403/385 |
| 7,931,677 B2 | 4/2011 | Abdelgany | |
| 8,216,240 B2 | 7/2012 | Dewey | |
| 8,246,625 B2 | 8/2012 | Miller et al. | |
| 8,608,782 B1 | 12/2013 | Rovner | |
| 8,636,776 B2 | 1/2014 | Rosenberg et al. | |
| 2004/0034350 A1* | 2/2004 | St. Onge | A61F 5/05 606/60 |
| 2007/0213715 A1* | 9/2007 | Bridwell | A61B 17/025 606/264 |
| 2012/0004659 A1* | 1/2012 | Miller | A61B 17/6466 606/54 |
| 2012/0221057 A1* | 8/2012 | Zhang | A61B 17/701 606/264 |
| 2015/0148849 A1* | 5/2015 | Abidin | A61B 17/708 606/279 |
| 2017/0156757 A1* | 6/2017 | Muniz | A61B 17/6425 |

* cited by examiner

*Primary Examiner* — Jan Christopher L Merene

(57) ABSTRACT

Rod link reducer assemblies, systems, and methods thereof. The rod link reducer assembly provides a manipulator rod having a first end, a second end, and an elongate body extending along a body axis between the first end and the second end. A post extends outwardly from the rod. A rod manipulating joint comprise an elongate joint rod extending along a joint rod axis, a first coupling clamp disposed along the joint rod, the first coupling clamp releasably connectable to the post, and a second coupling clamp disposed along the joint rod adjacent to and rotatable about the joint rod relative to the first coupling clamp. The second coupling clamp is releasably connectable to a shaft. A biasing member is adapted to bias the second clamp against the first clamp.

14 Claims, 6 Drawing Sheets

PRIOR ART — resection
Rod link reducer

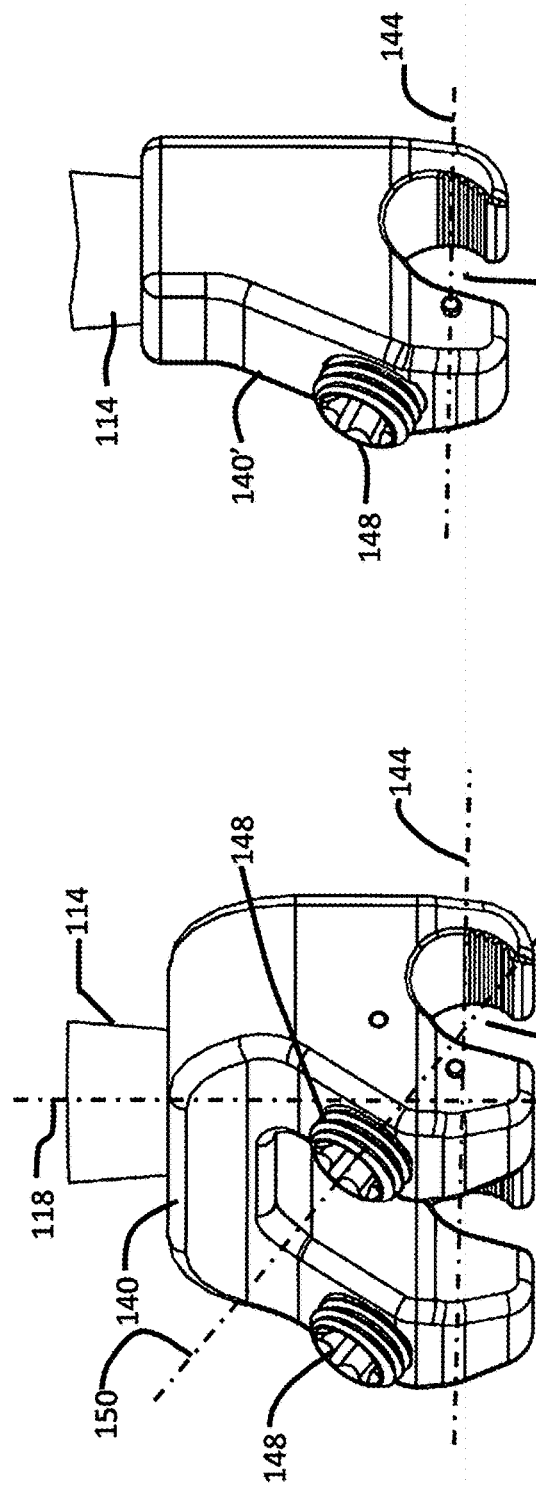
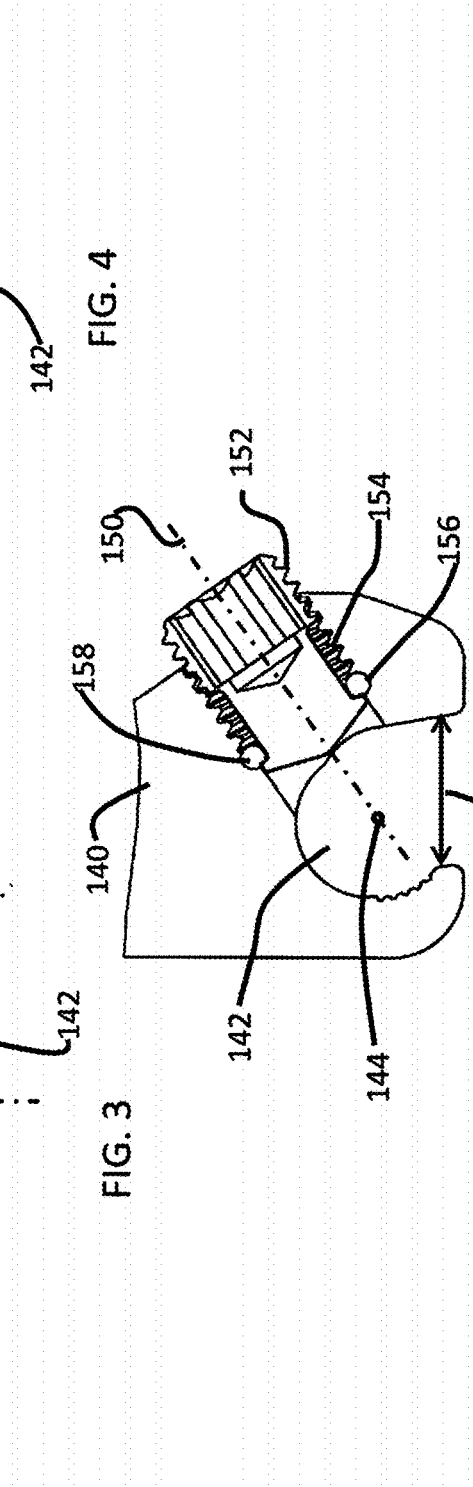
FIG. 3
FIG. 4
FIG. 5

ROD LINK REDUCER

CROSS REFERENCE TO RELATED APPLICATIONS

This patent application is a continuation of U.S. patent application Ser. No. 15/265,083, now U.S. Pat. No. 10,136,928 filed on Sep. 14, 2016 filed on Sep. 14, 2016, which is incorporated by its entirety herein.

FIELD OF THE INVENTION

The present invention relates to bone fixation, and more specifically, to a rod link reducer that can be used during the correction of spinal deformities.

DESCRIPTION OF THE RELATED ART

In severe spine deformity with coronal or sagittal decompensation, translation of the spinal column is necessary for restoration of trunk balance as well as deformity correction. However, the conventional correction methods, such as segmental reduction, global derotation, and apical translation, are usually unsatisfactory.

It would be beneficial to provide a rod link reducer assembly and method that provides a more direct and controlled approach to spinal correction.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a rod link reducer assembly may be configured to treat scoliosis. The rod link reducer assembly comprises a manipulator rod having a first end, a second end, and an elongate body extending along a body axis between the first end and the second end. A post extends outwardly from the rod. A rod manipulating joint comprise an elongate joint rod extending along a joint rod axis, a first coupling clamp disposed along the joint rod, the first coupling clamp releasably connectable to the post, and a second coupling clamp disposed along the joint rod adjacent to and rotatable about the joint rod relative to the first coupling clamp. The second coupling clamp is releasably connectable to a second post on a second manipulating rod. A biasing member is adapted to bias the second clamp against the first clamp.

Alternatively, a rod link reducer assembly comprises a manipulator rod having a first end, a second end, and an elongate body extending along a body axis between the first end and the second end. A handle is removably attachable to the first end of the manipulator rod. The handle is adapted to rotate the manipulator rod about the body axis. A tip is attached to the second end. The tip is sized to releasably receive and retain a rod inserted thereinto. A post extends outwardly from the rod between the first end and the second end. A rod manipulator joint is releasably attachable to the post. The rod manipulator joint comprises a joint rod, a first coupling clamp disposed along the joint rod and adapted to releasably retain the post, and a second coupling clamp disposed along the joint rod and rotatable relative to the first coupling clamp. A locking mechanism is adapted to releasably secure the first coupling clamp to the second coupling clamp.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 3 is a perspective view of a manipulating arm tip shown in the assemblies of FIG. 2;

FIG. 4 is an alternative embodiment of a manipulating arm tip that can be used in the assemblies of FIG. 2;

FIG. 5 is a sectional view of either of the manipulating arm tips shown in FIGS. 3 and 4;

DETAILED DESCRIPTION

Figure 1A:
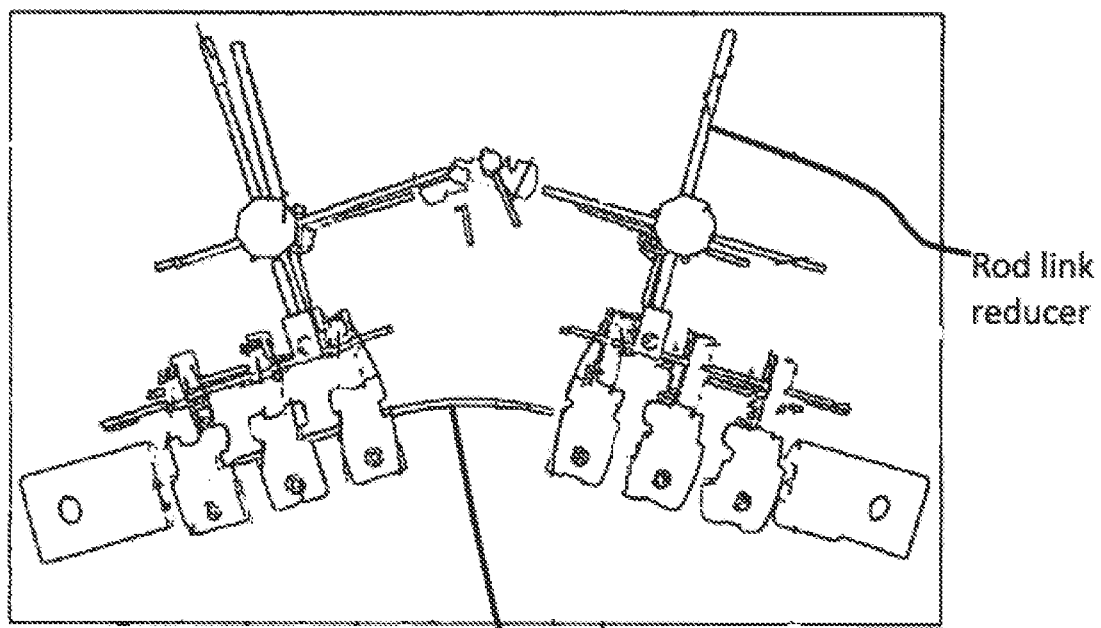
FIG. 1A is a rear elevational view showing prior art provisional rods and rod-link reducers correcting the sagittal curve.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Figure 1B:
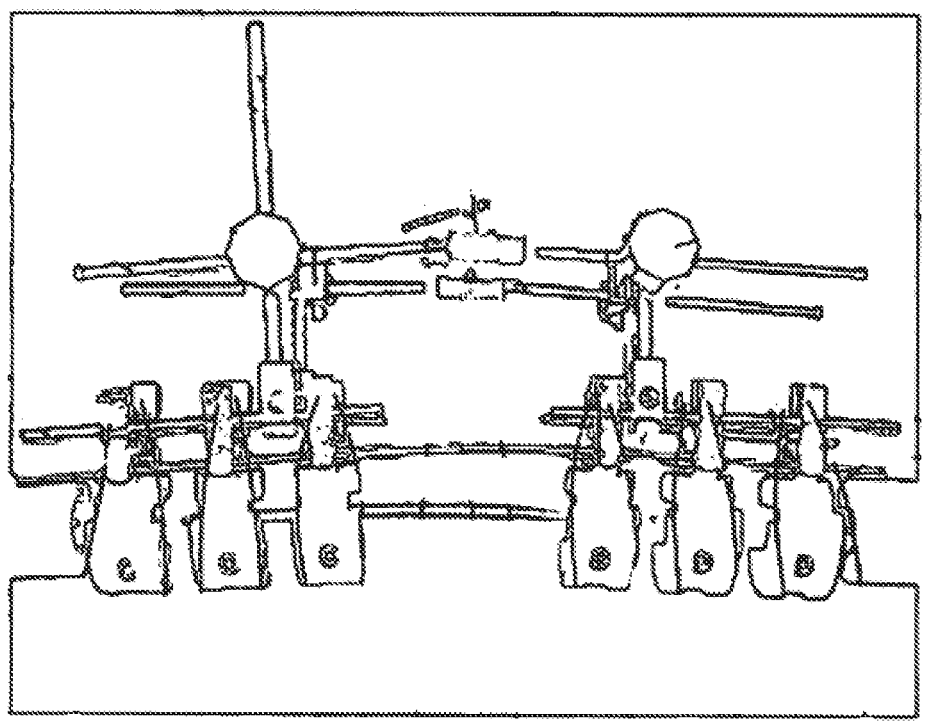
FIG. 1B is a rear elevational view showing prior art provisional rods and rod-link reducers for correcting the sagittal curve.

Severe scoliosis can be treated by using a technique known as reduction by a rod link reducer. In this procedure, shown in FIG. 1A, a rod link reducer is capable of manipulating a first temporary rod via a first manipulating arm and a second temporary rod via a second manipulating arm to temporarily correct a deformity. With the deformity temporarily corrected, a rod link is positioned between the first manipulating arm and second manipulating arm, whereby it is locked in place by tightening the first rod joint and the second rod joint. With the rod link in place, as shown in FIG. 1B, a permanent rod can then be placed on the opposite side of the spine to maintain the deformity correction.

Another known procedure includes a resection that is typically made in the vertebrae. The rod link reducer is used to manipulate the position of the vertebrae via fixation by temporary rods and the rod link. With the vertebrae manipulated into a desired anatomy, a permanent rod can be inserted thereby retaining the desired anatomy.

It would be beneficial to provide a rod link reducer assembly that permits simultaneous, controlled correction of a deformed spine in all planes of motion. In addition, it would be beneficial to provide a reducer with various tips that allow for the attachment of multiple rod sizes, allow for attachment around a screw head or between rods, and has a decreased profile.

The present disclosure provides embodiments of rod link reducer assemblies that can be used to alleviate severe scoliosis. According to one embodiment, a rod link reducer assembly may include two or more manipulating arms having a distinct rod gripping tip, and a manipulating joint having a locking mechanism.

Referring to FIGS. 2, 3, and 5-9, a rod link reducer assembly 100 ("reducer assembly 100") and a rod link reducer assembly 100' ("reducer assembly 100'") according to a first exemplary embodiment are shown. Reducer assembly 100 is connected to a rod 50 in an existing construct 52 and reducer assembly 100' is attached to a rod 50' in another existing construct 52'. While reducer assemblies 100, 100' are shown, because reducer assembly 100' is constructed from the same assembly components as reducer assembly 100, only reducer assembly 100 will be discussed in detail.

Assembly 100 is used to correct a spinal deformity by allowing the manipulation of temporary rods above and below the apex of the deformity to move the spine into a corrected state. The position of the rods is then locked and a permanent rod is then placed on the contralateral side of the spine to hold the correction.

Assembly 100 also permits simultaneous, controlled correction of a deformed spine in all planes of motion whereas prior art devices require multiple separate instruments for lateral-medial reduction, anterior-posterior reduction, and axial de-rotation. Assembly 100 simplifies such procedures and provides a new method of correcting simplex sagittal and kyphotic deformities.

In addition, assembly 100 can be provided with various tips that allow for the attachment of multiple rod sizes, allow for attachment around a screw head or between rods, and have a decreased profile. Manipulating arms of assembly 100 provide a more rigid coupling surface with the medial-lateral arm and an orientable attachment for a handle for surgeon preference. Assembly 100 can be disassembled and attached to the manipulating arm and provides sufficient angulation so that assembly 100 can be combined with translating arms to simplify the surgical procedure.

Figure 2:
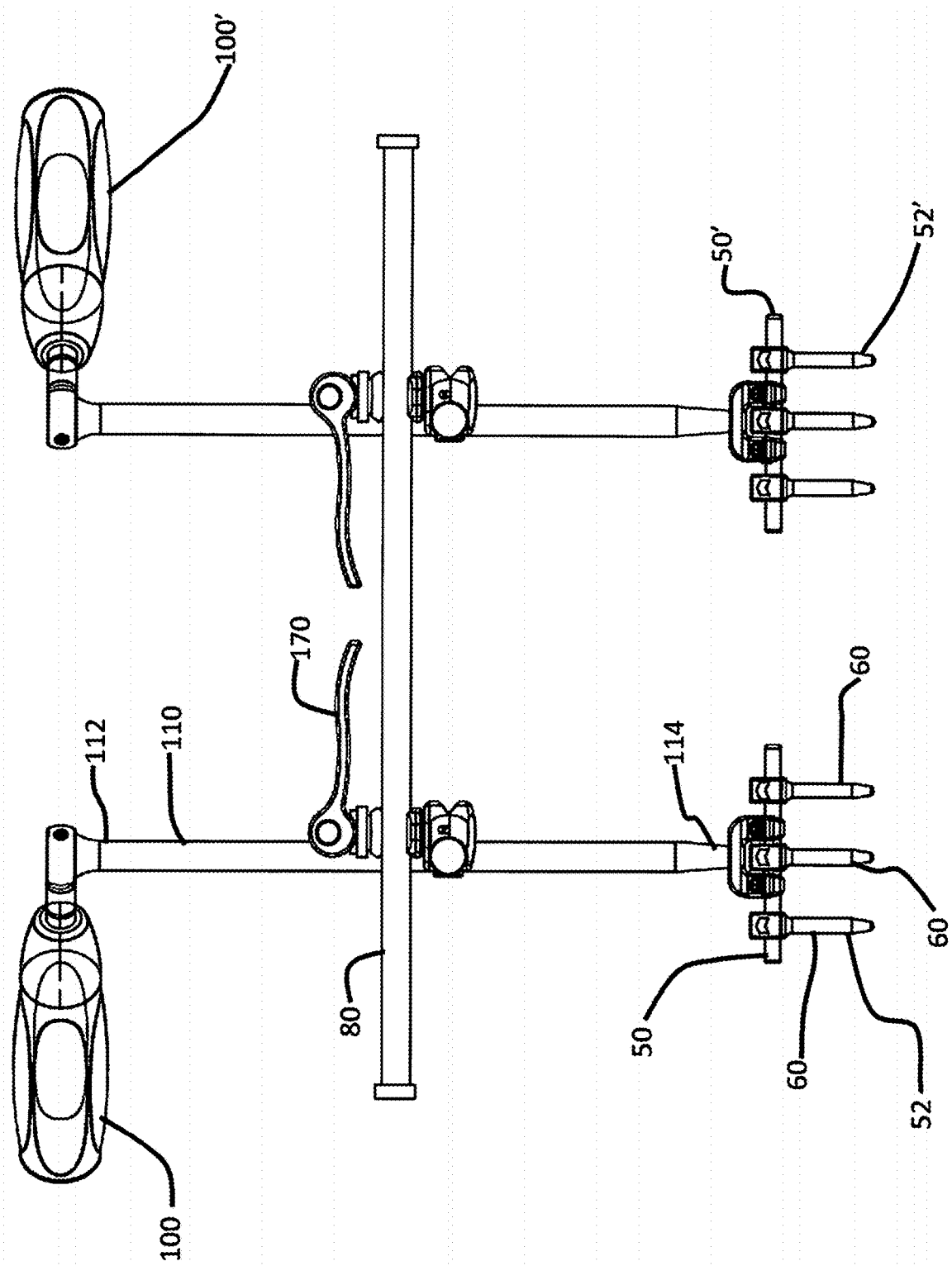
FIG. 2 is a perspective view of a pair of rod link reducer assemblies according to a first exemplary embodiment.
Figure 6:
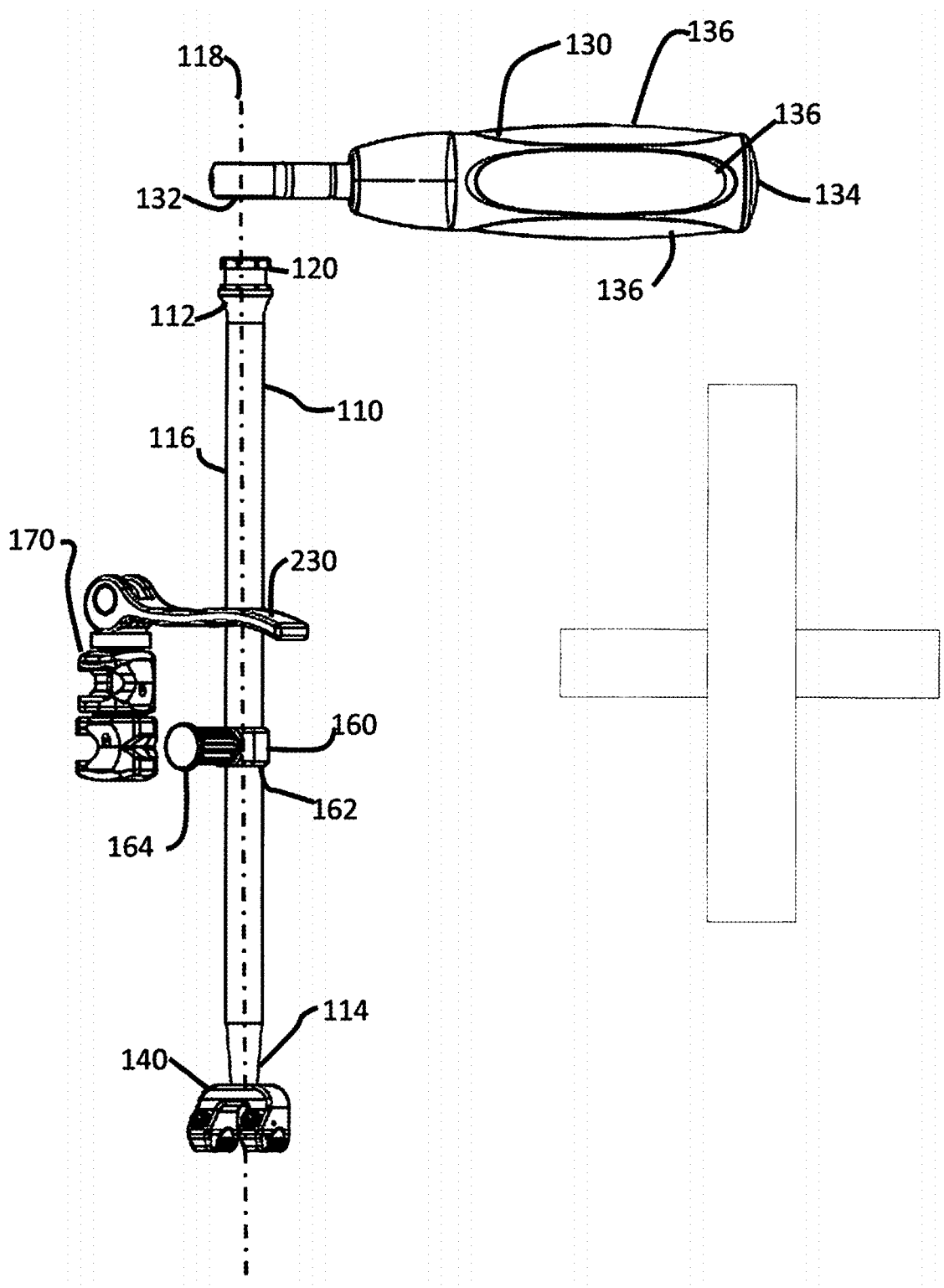
FIG. 6 is an exploded perspective view of one of the rod link reducer assemblies shown in FIG. 2.

Referring to FIGS. 2 and 6, assembly 100 includes a manipulator rod 110 having a first end 112, a second end 114, and an elongate body 116 extending along a body axis 118 between first end 112 and second end 114. First end 112 of manipulator rod 110 has a faceted interface 120.

A handle 130 is removably attachable to first end 112 of manipulator rod 110. Handle 130 is adapted to maneuver manipulator rod 110 as desired by the surgeon. Handle 130 has a faceted bore, or receiver, 132 adapted to receive faceted interface 120 of the first end. In an exemplary embodiment, faceted interface 132 has eight sides such that handle 130 can be rotated in 45 degree increments around manipulator rod 110 according to surgeon preference (e.g., right-handed or left-handed use) or to accommodate the patient's anatomy. While eight facets are disclosed, those skilled in the art will recognize that a different amount of facets, such as, six facets (allowing for rotation of handle 130 about manipulator rod 110 in 60 degree increments), can be used as well.

A free end 134 of handle 130 is sized to allow the surgeon to comfortably grip handle 130 for use. Free end 134 may include contours 136 to enhance the ergonomics of handle 130.

Referring now to FIGS. 2, 3, 5, and 6, second end 114 of manipulator rod 110 comprises a tip 140. Tip 140 comprises a receiver 142 adapted to releasably secure a construct 50 (shown in FIG. 2) therein. Tip 140 comprises a receiver axis 144 extending through receiver 142. In an exemplary embodiment, receiver axis 144 extends orthogonally to body axis 118. Tip 140 is sized to releasably receive and retain rod 50 inserted thereinto.

Receiver 142 has an opening 146 with a length "A" that is larger than the diameter of rod 50 to be inserted into receiver 142. To retain rod 50 within receiver 142, receiver 142 includes a securing member 148 extending along an axis 150 at an angle oblique to receiver axis 144. Securing member 148 includes a set screw 152 engaged with a threaded passage 154 and retainer pins 156, 158 located in passage 154 to prevent removal of set screw 152 from passage 154. The oblique angle of set screw 152 allows set screw 152 to be tightened from the contralateral side of the patient, resulting in less interference with the anatomy (e.g., running into facet joints). Pins 156, 158 retain set screw 152 while permitting sufficient motion to clamp a range of rod sizes.

Several different tip options are available for varying temporary rod diameters—a double tip 140 (shown in FIG. 3) can be provided to fit around a screw 60, as shown in FIG. 2. In an alternative embodiment, a single tip 140' (shown in FIG. 4) can be provided to fit between two screws.

Regardless of whether tip 140 or tip 140' is used, rod 50 is accepted into tip 140, 140' via opening 146, thereby allowing tip 140, 140' to be inserted downwardly onto rod 50 as viewed in FIG. 2, and secured to rod 50 by tightening set screw 152 against rod 50.

Referring now to FIG. 6, a post 160 extends outwardly from manipulator rod 110 between first end 112 and second end 114. In an exemplary embodiment, post 160 is a medial-lateral post. Post 160 is fixedly connected to manipulator arm 110 and is used to improve the ease of connection of rod manipulating joints onto manipulator rod 110 and to improve the rigidity of assembly 100. Post 160 allows for intraoperative versatility of assembly 100 to affix manipulator rod 110 and shaft 80 in desirable orientations. Further, the orientation of post 160 allows for a clamp to clamp thereon, as will be discussed in detail below, so that assembly 100 can be more rigid in the direction where a corrective force on the patient's spine is required. Alternatively, rod manipulating joints can be connected directly to manipulator rod 110.

Post 160 has a connected end 162 that is connected to manipulator rod 110 and a free end 164 having a larger cross-section than connected end 162. In an exemplary embodiment, post 160 has a generally cylindrical cross section, and second end 164 can be outwardly flared to prevent a connection thereon from sliding off post 160.

Figure 7:
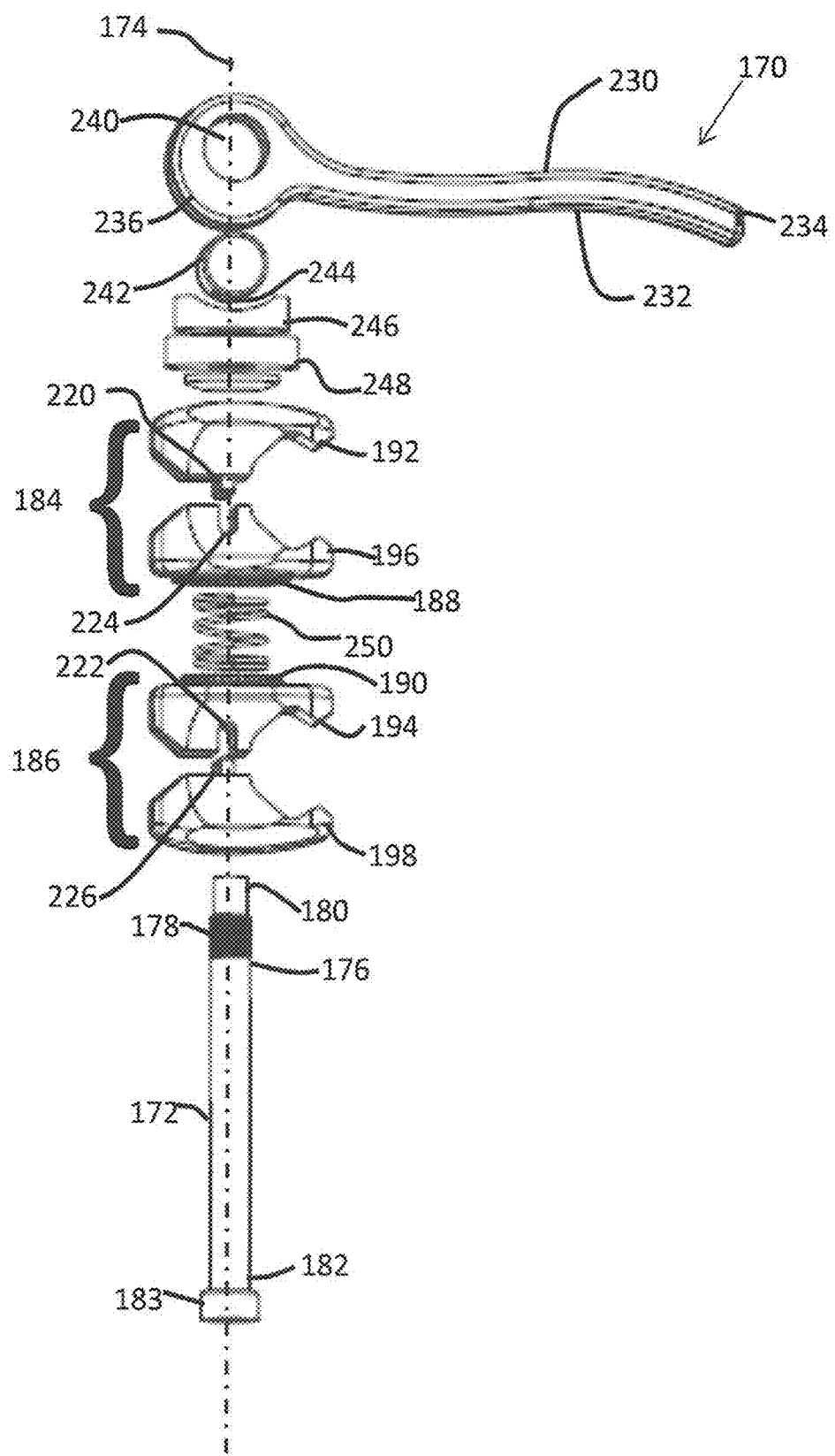
FIG. 7 is an exploded perspective view of rod manipulator joint used in the rod link reducer assembly of FIG. 6.
Figure 8:
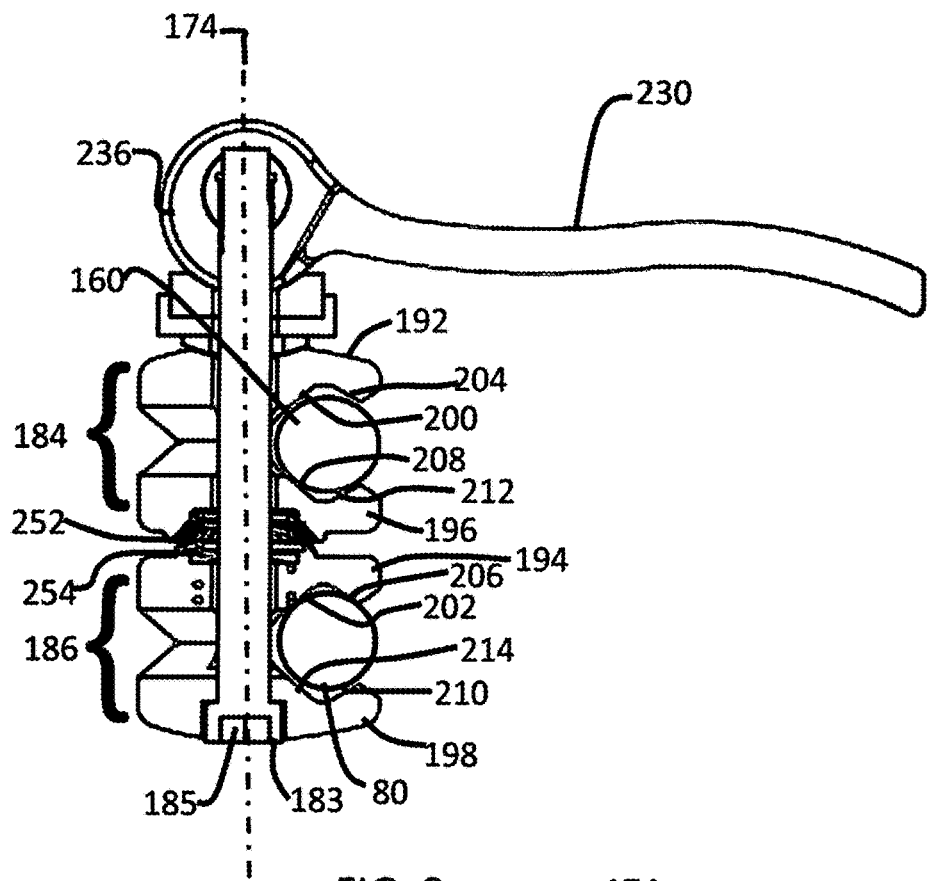
FIG. 8 is a side elevational view, in section, of the assembled rod manipulator joint shown in FIG. 7, in a compressed condition.
Figure 9:
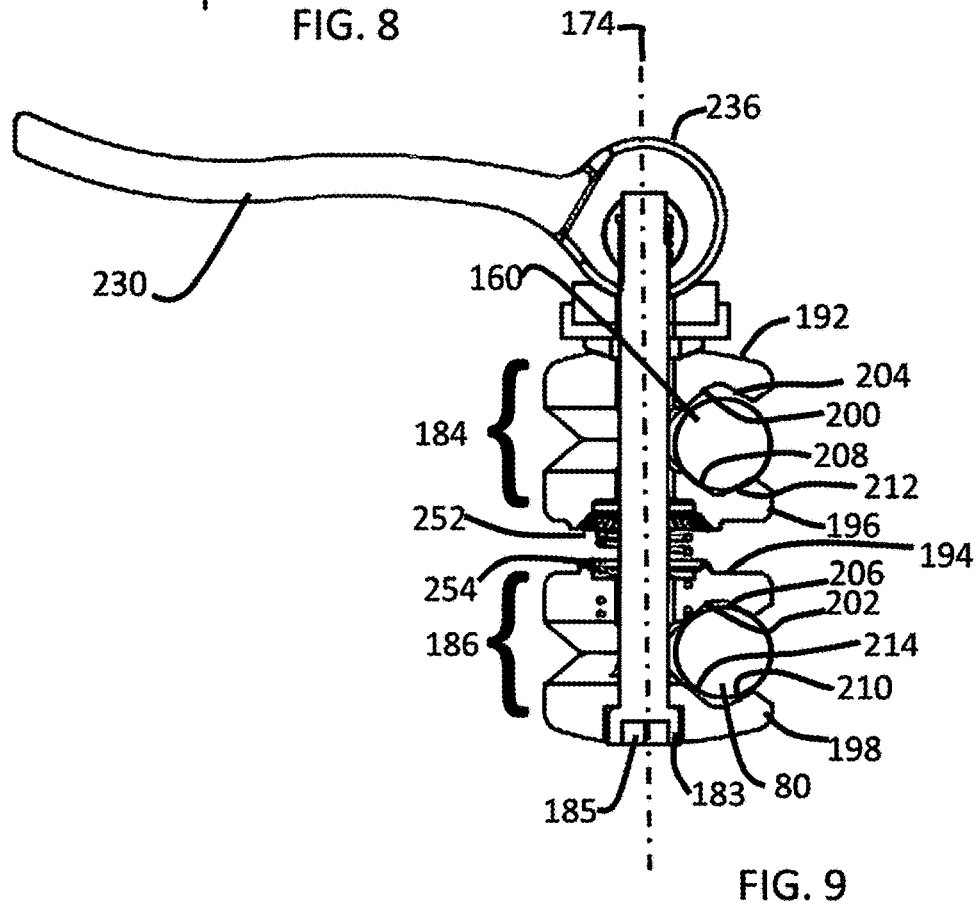
FIG. 9 is a side elevational view, in section, of the assembled rod manipulator joint shown in FIG. 7, in an uncompressed condition.

Referring now to FIGS. 6-9, a rod manipulator joint 170 is releasably attachable to post 160. Rod manipulator joint 170 includes an elongate joint rod 172 that extends along a joint rod axis 174. Joint rod 172 includes a superior end 176 that has a threaded portion 178 that is disposed inferiorly of a superior tip 180. An inferior end 182 includes a cap 183 that prevents elements on joint rod 172 from sliding off joint rod 172. As shown in FIGS. 8 and 9, cap 183 includes an internal hex 185 allows a tool (not shown) to be inserted therein to secure joint rod 172 within rod manipulator joint 170. Joint rod 172 prevents disassembly of rod manipulator joint 170 and maintains axial alignment of the components of rod manipulator joint 170.

Rod manipulator joint 170 also includes a first coupling clamp 184 disposed along joint rod 172. First coupling clamp 184 is releasably connectable to post 160. While first coupling clamp 184 is separate from manipulator rod 110, those skilled in the art will recognize that first coupling clamp 184 can be integrated with manipulator rod 110, such as is disclosed in U.S. Patent Application Publication No. 2012/0221057, which is incorporated herein by reference, thereby making such an assembly quicker to assemble, less fidgety, and more rigid.

A second coupling clamp 186 is disposed along joint rod 172 adjacent to and rotatable about joint rod axis 174 relative to first coupling clamp 184. Second coupling clamp 186 is releasably connectable to a shaft, such as shaft 80 shown in FIG. 2. While first coupling clamp 184 is shown coupled to post 160 and second coupling clamp 186 is shown coupled to shaft 80, those skilled in the art will recognize that first coupling clamp 184 can be coupled to shaft 80 and second coupling clamp 186 can be coupled to post 160, depending on the anatomy of the patient and the type of spinal correction required.

First coupling clamp 184 comprises a first coupler end 188 and second coupling clamp 186 comprises a second coupler end 190 that is adapted to releasably engage first coupler end 188, thereby restricting rotation of the first coupling clamp with respect to the second coupling clamp. Coupler ends 188, 190 can be mating star grind surfaces that are engageable with each other to restrict rotation of coupling clamps 184, 186 with respect to each other.

Each of first coupling clamp 184 and second coupling clamp 186 includes a superior clamp portion 192, 194, respectively, and an inferior clamp portion 196, 198, respectively, that is movable along joint rod axis 174 relative to respective superior clamp portions 192, 194. Referring specifically to FIG. 9, each superior clamp portion 192, 194 comprises a first clamping surface 200, 202, respectively, extending at a first angle oblique to joint rod axis 174 and a second clamping surface 204, 206, respectively extending at a second angle oblique to joint rod axis 174. Similarly, each inferior clamp portion 196, 198 comprises a first clamping surface 208, 210, respectively, extending at a first angle oblique to joint rod axis 174 and a second clamping surface 212, 214, respectively extending at a second angle oblique to joint rod axis 174. The clamping surfaces on each clamp portion 192-198 form generally "V-shaped" surfaces that provide four lines of contact with their respective post 160 or shaft 80, as shown in FIG. 8.

Referring back to FIG. 7, each superior clamp portion 192, 194 includes one of a tab 220 and a slot 222, while each inferior clamp portion 196, 198 includes the other of a slot 224 and a tab 226 such that each tab 220, 226 engages a respective slot 222, 224 and prevents rotation of superior clamp portion 192, 194 relative to its inferior clamp portion 196, 198.

A first biasing member in the form of a clamp 230 is adapted to releasably secure and bias second coupling clamp 186 against first coupling clamp 184. Clamp 230 includes a lever 232 having a free end 234 and a cam 236, distal from free end 234, that is rotatably connected to joint rod 172. Cam 236 allows for quick release of coupling clamps 184, 186 when desired.

Cam 236 is operable between a secure position wherein first coupling clamp 184 is non-rotatable relative to second coupling clamp 186 (as shown in FIG. 7) and a released position wherein first coupling clamp 184 is rotatable relative to second coupling clamp 186 (as shown in FIG. 8).

Cam 236 includes a passage 240 through which a cam axle 242 extends. Cam axle 242 includes a transverse threaded passage 244 that is threaded onto threaded portion 178 of joint rod 172 to secure lever 232 onto joint rod 172. Passage 240 is off-center within cam 236 such that, as lever 234 is rotated between the positions shown in FIGS. 8 and 9, cam 236 alternates between a secure position and a release position. When cam 236 is in the secure position, first coupling clamp 184 securely engages post 160 and when cam 236 is in the released position, first coupling clamp 184 is removable from post 160. Cam 236 engages a concave cam surface 246, which transmits the compressive action of cam 236 to a washer 248 on which first coupling clamp 184 pivots.

Rod manipulating joint 170 further includes a second biasing member in the form of a helical spring 250 that is located between first coupling clamp 184 and second coupling clamp 186. Spring 250 is adapted to bias first coupling clamp 184 away from second coupling clamp 186 when cam 236 is in the release position to allow for the insertion and/or removal of post 160 and shaft 80.

Inferior clamp portion 196 of first coupling clamp 184 includes a superior recess 252 and superior clamp portion 194 of second coupling clamp 186 includes an inferior recess 254 that receive spring 250 when rod manipulating joint 170 is in the secure position.

To use assembly 100, tip 140 (or 140') is inserted over rod 60 that is already part of a construct that is attached to a patient and set screw 146 is tightened to secure tip 140 to rod 60. Handle 130 is inserted over first end 112 of manipulator rod 110 and rotated about rod axis 118 to locate post 160 in a desired position relative to the anatomy of the patient.

With lever 232 rotated to the release position, as shown in FIG. 9, first and second coupling clamps 184, 186 are open sufficiently to allow first coupling clamp 184 to be inserted over post 160. Additionally, both first and second coupling clamps 184, 186 can be rotated relative to joint rod 172 and to each other to accommodate the anatomy of the patient. Shaft 80 can be inserted into second coupling clamp 186 and lever 232 can be rotated to the position shown in FIG. 8, forcing cam 236 downward, locking post 160 within first coupling clamp 184, shaft 80 within second coupling claim 186, and engaging star grind surfaces of coupler ends 188, 190 to restrict rotation of first and second coupling clamps 184, 186.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A rod link reducer assembly comprising:
   a manipulator rod having a first end, a second end, and an elongate body extending along a body axis between the first end and the second end;
   a handle removably and traversely attached to the first end of the manipulator rod;
   a post extending outwardly from the rod; and
   a rod manipulating joint comprising:
      an elongate joint rod extending along a joint rod axis;
      a first coupling clamp disposed along the joint rod, the first coupling clamp releasably connectable to the post;
      a second coupling clamp disposed along the joint rod adjacent to and rotatable about the joint rod relative to the first coupling clamp, the second coupling clamp releasably connectable to a second post;
      a lever having a free end and a cam, distal from free end, that is rotatably connected to the joint rod, and
      a first biasing member adapted to bias the second clamp against the first clamp,
   at least two screw assemblies, a construct adapted to extend between the at least two screw assemblies, the two screw assemblies each include a screw and a housing, where the housing is adapted to receive a rod of the construct,
   wherein the second end of the manipulator rod comprises a tip, the tip comprising a receiver adapted to releasably secure the construct therein and a receiver axis extending orthogonally to the body axis,
   wherein the receiver further comprises a securing member to releasably secure the construct to the receiver, the securing member extending at an angle oblique to the receiver axis,
   wherein the handle is configured to rotate the receiver about the receiver axis to align the rod of the construct, the handle having a free end to allow a user to grip the handle.

2. The rod link reducer assembly according to claim 1, wherein the first end of the manipulator rod comprises a faceted interface.

3. The rod link reducer assembly according to claim 2, wherein the handle includes a faceted receiver adapted to receive the faceted interface of the first end.

4. The rod link reducer assembly according to claim 1, wherein the post has a cylindrical cross-section.

5. The rod link reducer assembly according to claim 1, wherein the post has a connected end connected to the manipulator rod and a free end having a larger cross-section than the connected end.

6. The rod link reducer assembly according to claim 1, wherein each of the first coupling clamp and the second coupling clamp comprises a superior clamp portion and an inferior clamp portion movable along the joint rod relative to the superior clamp portion.

7. The rod link reducer assembly according to claim 6, wherein each superior clamp portion comprises a first clamping surface extending at a first angle oblique to the joint rod axis and a second clamping surface extending at a second angle oblique to the joint rod axis.

8. The rod link reducer assembly according to claim 6, wherein the superior clamp portion of the first coupling clamp comprises one of a tab and a slot and wherein the inferior clamp portion of the first coupling clamp comprises the other of a tab and a slot such that the tab engages the slot and prevents rotation of the superior clamp portion relative to the inferior clamp portion.

9. The rod link reducer assembly according to claim 1, wherein the first coupling clamp comprises a first coupler end and wherein the second coupling clamp comprises a second coupler end adapted to releasably engage the first coupler end thereby restricting rotation of the first coupling clamp with respect to the second coupling clamp.

10. The rod link reducer assembly according to claim 1, wherein the rod manipulating joint further comprises a second biasing member located between the first coupling clamp and the second coupling clamp, the second biasing member being adapted to bias the first coupling clamp away from the second coupling clamp.

11. The rod link reducer assembly according to claim 1, wherein the cam is operable between a secure position wherein the first coupling clamp is non-rotatable relative to the second coupling clamp and a released position wherein the first coupling clamp is rotatable relative to the second coupling clamp.

12. A rod link reducer assembly comprising:
   a manipulator rod having a first end, a second end, and an elongate body extending along a body axis between the first end and the second end;
   a handle removably and transversely attachable to the first end of the manipulator rod, the handle being adapted to rotate the manipulator rod about the body axis;
   a post extending outwardly from the rod between the first end and the second end; and
   a rod manipulator joint releasably attachable to the post, the rod manipulator joint comprising:
      a joint rod;
      a first coupling clamp disposed along the joint rod and adapted to releasably retain the post;
      a second coupling clamp disposed along the joint rod and rotatable relative to the first coupling clamp;

a lever having a free end and a cam, distal from free end, that is rotatably connected to the joint rod and a locking mechanism adapted to releasably secure the first coupling clamp to the second coupling clamp, at least two screw assemblies, a construct adapted to extend between the at least two screw assemblies, the two screw assemblies each include a screw and a housing, where the housing is adapted to receive a rod of the construct, wherein the second end of the manipulator rod comprises a receiver configured to releasably secure the construct, wherein the receiver comprises a set screw to releasably secure the construct, the set screw engaged with a threaded passage, wherein the handle is configured to rotate the receiver about a receiver axis to align the rod of the construct, the handle having a free end to allow a user to grip the handle.

13. The rod link reducer assembly according to claim 12, wherein the locking mechanism comprises a cam lever attached to the joint rod.

14. A rod link reducer assembly comprising:
a manipulator rod comprising:
a first end comprising a faceted interface;
a second end comprising a tip; and
an elongate body extending along a body axis between the first end and the second end;
a handle removably and transversely attachable to the first end of the manipulator rod, the handle having a receiver adapted to receive the faceted interface of the first end;
a post having a connected end extending outwardly from the rod between the first end and the second end and a free end having a cross-section larger than the connected end; and
a rod manipulator joint releasably attachable to the post, the rod manipulator joint comprising:
a joint rod;
a first coupling clamp disposed along the joint rod and adapted to releasably retain the post;
a second coupling clamp disposed along the joint rod and rotatable relative to the first coupling clamp;
a biasing member disposed between the first coupling clamp and the second coupling clamp; and
a lever having a free end and rotatably connected to the joint rod,
a cam locking mechanism adapted to releasably secure the first coupling clamp to the second coupling clamp,
at least two screw assemblies, a construct adapted to extend between the at least two screw assemblies, the two screw assemblies each include a screw and a housing, where the housing is adapted to receive a rod of the construct,
wherein the tip comprises a set screw engaged with a threaded passage,
the tip further comprising a receiver adapted to releasably secure the construct therein via the set screw,
wherein the handle is configured to rotate the receiver about a receiver axis to align the rod of the construct, the handle having a free end to allow a user to grip the handle.

\* \* \* \* \*